United States Patent [19]
Jeffery et al.

[11] 4,102,655
[45] Jul. 25, 1978

[54] BUBBLE TRAP

[75] Inventors: Russell L. Jeffery, Littleton, Colo.; Lawrence V. Cote, Ronan, Mont.

[73] Assignee: Cobe Laboratories, Inc., Lakewood, Colo.

[21] Appl. No.: 792,793

[22] Filed: May 2, 1977

[51] Int. Cl.² .............................................. A61M 1/03
[52] U.S. Cl. ................... 55/201; 210/188; 210/321 B
[58] Field of Search ............. 128/214 R; 23/258.5 A, 23/258.5 M; 55/201; 210/188, 321 B, 96 M, 22, 94; 137/170.1, 203, 176, 177, 179, 197

[56] References Cited

U.S. PATENT DOCUMENTS

| | | | |
|---|---|---|---|
| 927,476 | 7/1909 | Barker | 55/201 |
| 3,295,297 | 1/1967 | Collins | 55/178 |
| 3,598,727 | 8/1971 | Willock | 210/321 B X |
| 3,827,561 | 8/1974 | Serfass et al. | 210/321 B X |

OTHER PUBLICATIONS

Galletti et al., "Heart Lung Bypass–Principles and Techniques of Extracorporeal Circulation", 1962, Grune & Stratton, pp. 156–159.

*Primary Examiner*—Frank A. Spear, Jr.

[57] ABSTRACT

A bubble trap comprising a closed container for holding liquid, an inlet extending through the container bottom upward within the container to an inlet opening spaced below the container top, the container having a larger cross-sectional area exclusive of the inlet than the inlet itself, an outlet extending through the container top downward within the container to an outlet opening, the outlet opening being lower in the container than the inlet opening whereby liquid flowing upward through the inlet opening into the container must subsequently flow downward to reach the outlet opening, and means for admitting or removing gas from the container.

7 Claims, 1 Drawing Figure

U.S. Patent July 25, 1978 4,102,655
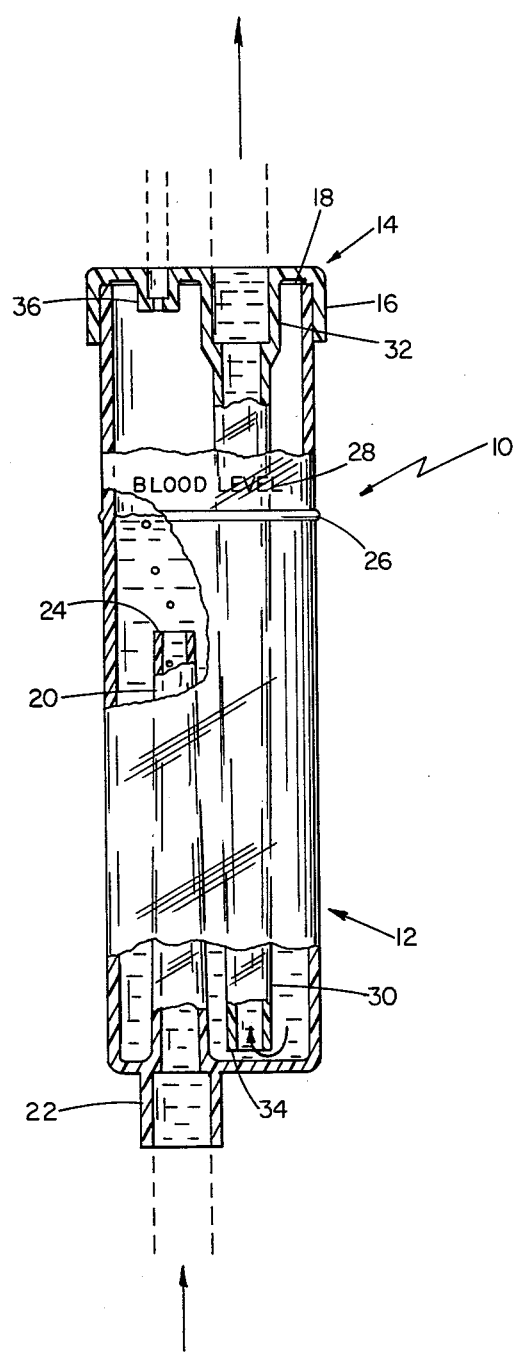

BUBBLE TRAP

FIELD OF THE INVENTION

This invention relates to removing gas bubbles from liquids such as blood that is withdrawn from the body for hemodialysis.

BACKGROUND OF THE INVENTION

When it has been desirable or necessary to remove gas bubbles from liquids flowing in closed systems, the art has employed devices known as bubble traps. One such need for a bubble trap has been removal of air bubbles from blood flowing extracorporeally through a dialyzer. A leak in the system where it is under negative pressure may cause such air bubble formation.

One method of bubble removal used in some bubble traps is to let the momentum of upflowing liquid carry the bubbles to the surface where they are expelled. The outlet is positioned away from the liquid surface to receive debubbled liquid.

It would also be desirable to slow down the flow of liquid toward the outlet and thereby reduce the drag of the liquid on the entrapped bubbles that do not immediately reach the surface so that such bubbles will be more likely to reach the surface by their own buoyancy. One way to slow down the flow is to increase the area of the flow passage toward the outlet.

Another desirable feature for a bubble trap is an ability to be connected in-line into a system (i.e., the trap can simply replace a section of the fluid line, without the need for alterations in the plumbing, including introducing bends in the lines with the possibility of kinks under negative pressure).

Finally, a bubble trap that could serve the added purpose of monitoring blood pressure would be desirable, particularly if it were not necessary actually to introduce blood into the pressure monitoring circuit.

Serfass et al. U.S. Pat. No. 3,827,561 shows a dialysate head vessel having a submerged riser of smaller diameter than that of the vessel itself and an outlet apparently coming out the vessel bottom. Bubbles rise with inlet flow, but no way is shown for an in-line connection of the vessel. In Galletti et al., *Heart-Lung Bypass—Principles and Techniques of Extracorporeal Circulation* (1962, Grune and Stratton), the device shown in FIG. 53A (p. 156) operates in an initially upflow mode, but, if anything, there is a decrease in flow passage area as the blood cascades toward the outlet, and the device is not connected in-line, for the inlet and outlet are at right angles. Finally, Collins U.S. Pat. No. 3,295,297 shows a device that is closer to having an in-line connection, but its outlet is positioned near the blood surface.

SUMMARY OF THE INVENTION

We have discovered that the problems of bubble entrapment, kinking in liquid lines, and presence of liquid in a pressure monitoring circuit can be solved by providing a bubble trap comprising a closed container for holding liquid, an inlet extending through the container bottom upward within the container to an inlet opening spaced below the container top, the container having a larger cross-sectional area than the inlet, an outlet extending through the container top downward within the container to an outlet opening, the outlet opening being lower in the container than the inlet opening whereby liquid flowing upward through the inlet opening into the container must subsequently flow downward to reach the outlet opening, and means for admitting or removing gas from the container. This bubble trap is effective in bubble removal, is easy to make, has few parts, and can be readily connected in-line in a liquid flow system.

In particular aspects the bubble trap includes a plastic container that is a cylinder having a closed bottom end and an open upper end covered by a circular cap. An inlet in the form of a tube is formed in the closed bottom end, and an outlet in the form of a tube extending almost to the bottom of the container is formed in the cap, as is the gas admitting or removing means which is a tube for permitting pressure monitoring and adjustment of liquid level.

PREFERRED EMBODIMENT

We turn now to description of a presently-preferred embodiment of the invention.

DRAWING

There is shown in the single FIGURE a view in front elevation, partially in vertical cross section, of said embodiment.

DESCRIPTION

The embodiment shown in the drawing and its operation are now described.

Embodiment

The FIGURE shows bubble trap 10, which is a cylindrical container of transparent polyvinyl chloride plastic and is made from two injection molded pieces, body 12 and cap 14, solvent bonded together between the inner surface of skirt 16 of cap 14 and the outer surface of body 12 adjacent its open end and between the upper edge of body 12 and inner circular ridge 18 of cap 14.

Body 12 has an upwardly extending inlet comprising internally formed tapered tube 20 and externally formed counterbored sleeve 22, the latter for receiving blood tubing (indicated in broken lines). Mouth 24 of tube 20 is about ½ inch below external raised ring 26, which in conjunction with indicia 28 marks the recommended blood level. Cap 14 has a downwardly extending outlet comprising tapered tube 30 and counterbored base 32, the latter, as with sleeve 22, for receiving blood tubing (indicated in broken lines). Mouth 34 of tube 30 is about ⅛ inch above the closed end of body 12; cap ridge 18 helps to predetermine accurately that spacing. Also formed in cap 14 is tube 36 having a counterbored upper portion for receiving air tubing (indicated in broken lines).

As to other dimensions of the bubble trap, body 12 is 3 13/32 inches long and about 27/32 inch in inner diameter, and its wall is about 3/64 inch thick. Inlet tube 20 is about 1 7/8 inches long, and has an inner diameter of about ⅛ inch at mouth 24. sleeve 22 is about ⅝ inch long with an inner diameter of ¼ inch. Tube 30 and base 32 are together 3⅝ inches long. The inner diameter at mouth 34 is ⅛ inch, and the inner diameter of base 32 is ¼ inch. Tube 36 is 3/16 inch long; its bore is 1/16 inch in diameter, and its counterbore is about ⅛ inch in diameter.

Operation

Bubble trap 10 is connected into a hemodialyzer system as follows. Blood tubing connected to withdraw blood from a patient (arterial side) is solvent bonded into inlet sleeve 22. Likewise, blood tubing connected to return blood to the patient is solvent bonded into outlet base 32. Between outlet base 32 and the patient on the downstream side are, first, a positive displacement blood pump (not shown), then the hemodialyzer (not shown), and then another bubble trap (not shown; it is not like trap 10 but is of the conventional downflow, drip chamber variety). Air tubing is solvent bonded into tube 36 in cap 14, and leads by a Y-connection to both a manual air pump and a pressure monitoring device (neither shown). A clamp (not shown) upstream of inlet sleeve 22 maintains the upstream blood tubing in position, and the displacement pump itself maintains the blood tubing leading from outlet base 32 in position.

In operation, blood from the patient is drawn by negative pressure (from 100 to 200 mmHg) relative to atmospheric and blood pressure into bubble trap 10, entering through sleeve 22, passing through tube 20, and flowing out of mouth 24 into body 12, which has a much larger cross-sectional area than tube 20. Blood fills body 12 up to ring 26, and the blood level is maintained there by being raised or lowered as necessary by the manual air pump. The blood is then drawn by the blood pump into outlet tube 30 through mouth 34 and travels upward through outlet base 32 and out of the bubble trap. It then flows through the blood tubing, the pump (which drives the blood on with 200 to 300 mmHg positive pressure), the hemodialyzer, and the second bubble trap and back to the patient. Blood flow rate is from 50 to 350 ml/min.

Should a leak occur between where the blood is taken from the patient and inlet sleeve 22, air may enter the blood in the form of a bubble or bubbles because of the negative pressure in the blood tubing in that part of the loop. The bubble or bubbles will enter bubble trap 10 and be carried upward by the incoming blood toward the surface of the blood at ring 26. Most bubbles because of the force imparted by the blood will reach the surface and enter the gaseous atmosphere above the blood. If a bubble does not reach the surface, it will tend to be carried downward by the blood as it flows toward outlet mouth 34, but because of the increase in cross-sectional area from inlet tube 20 to body 12, the blood flow downward will be slower and there will consequently be less drag on the bubbles and more opportunity for them to reach the surface due to their own buoyancy. Hence the blood entering outlet mouth 34 at the bottom of body 12 should be free of most of the bubbles.

The pressure monitoring device connected to tube 36 monitors blood pressure upstream of the blood pump, and will sound an alarm and stop the blood pump if the pressure of the air (and of the blood) becomes too negative, thereby preventing damage to a blood vessel at the needle site from excessive negative pressure.

At the end of dialysis, because outlet mouth 34 is so close to the bottom of body 12, almost all the blood in the bubble trap can be withdrawn from it and returned to the patient.

Body 12 is sized and ring 26 positioned to handle sudden shifts either from negative pressure to positive pressure in the inlet line (when, e.g., the blood pump is stopped) or from positive pressure to negative pressure (e.g., when the pump starts up). In the former instance the air space above ring 26 allows for further filling of body 12 with blood before blood can pass through tube 36 into the pressure monitoring circuit. In the latter instance, the blood level can be lowered from ring 26 quite far without uncovering outlet mouth 34 and drawing air into the outlet line.

Conclusion

Other embodiments and uses are within the scope of the invention and claims.

What is claimed is:

1. A bubble trap for blood comprising:
a closed transparent container for holding blood,
said container having a top and a bottom and indicium constituting a blood level indicator,
an inlet tube into said container,
said inlet tube entering through said container bottom and extending upward within said container to an inlet opening and said inlet opening having a cross-sectional area smaller than the flow cross-sectional area of said container,
said inlet opening being spaced below said container top and below said indicium to direct gas bubbles toward said indicium,
an outlet tube from said container exiting through said container top,
said outlet tube extending downward into said container to an outlet opening,
said outlet opening being lower in said container than said inlet opening whereby blood flowing upward through said inlet opening into said container must subsequently flow downward to reach said outlet opening, and
means positioned in the top of the container for removing gas from said container.

2. The bubble trap of claim 1 wherein said outlet opening is positioned adjacent to but spaced from the bottom of said container.

3. The bubble trap of claim 2 wherein said container is a cylinder having a closed bottom end and said container top is a circular cap covering the upper open end of said cylinder.

4. The bubble trap of claim 2 wherein said inlet opening is about 1⅞ inches above said container bottom and said outlet opening is about ⅛ inch above said bottom, said container is a cylinder with an inner diameter of about 27/32 inch and said inlet opening has a diameter of about ⅛ inch.

5. The bubble trap of claim 3 wherein said means for removing gas is a tube in said cap and said tube permits adjusting the level of blood in said container and monitoring pressure in said container.

6. The bubble trap of claim 3 wherein said container is made of plastic, said outlet tube is integrally formed with said cap, and said inlet tube is integrally formed with said cylinder bottom end.

7. The bubble trap of claim 6 wherein said inlet tube and said outlet tube are counterbored at the ends opposite their respective said openings, for receiving and connecting with blood tubing.

* * * * *